US010853679B2

(12) United States Patent
Tanaka et al.

(10) Patent No.: US 10,853,679 B2
(45) Date of Patent: Dec. 1, 2020

(54) MONITORING ASSISTANCE SYSTEM, CONTROL METHOD THEREOF, AND PROGRAM (71) Applicant: Omron Corporation, Kyoto (JP)

(72) Inventors: Kiyoaki Tanaka, Shiga (JP); Jumpei Matsunaga, Tokyo (JP); Shinji Takahashi, Shiga (JP); Tatsuya Murakami, Shiga (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 16/463,119

(22) PCT Filed: Nov. 28, 2017

(86) PCT No.: PCT/JP2017/042584
§ 371 (c)(1),
(2) Date: May 22, 2019

(87) PCT Pub. No.: WO2018/159040
PCT Pub. Date: Sep. 7, 2018

(65) Prior Publication Data
US 2020/0065600 A1 Feb. 27, 2020

(30) Foreign Application Priority Data
Mar. 2, 2017 (JP) ................................. 2017-039319

(51) Int. Cl.
G06K 9/20 (2006.01)
G06T 7/73 (2017.01)
G06K 9/46 (2006.01)

(52) U.S. Cl.
CPC .......... *G06K 9/2054* (2013.01); *G06K 9/209* (2013.01); *G06K 9/4609* (2013.01); *G06T 7/73* (2017.01);
(Continued)

(58) Field of Classification Search
CPC ........... G08B 25/04; G08B 25/00; G06T 7/11; G06T 7/73; G06T 2207/30196;
(Continued)

(56) References Cited

U.S. PATENT DOCUMENTS

2013/0182092 A1 7/2013 Ishii et al.
2013/0215248 A1 8/2013 Ishii et al.
(Continued)

FOREIGN PATENT DOCUMENTS

JP H11-99140 A 4/1999
JP 2006-133941 A 5/2006
(Continued)

OTHER PUBLICATIONS

International Search Report issued in Application No. PCT/JP2017/042584, dated Feb. 20, 2018 (1 page).
(Continued)

*Primary Examiner* — Neil R Mikeska
(74) *Attorney, Agent, or Firm* — Osha Liang LLP (57) ABSTRACT In a watching assistance system that assists watching over a subject on a bed, a region setting unit performs processing of receiving a region setting image captured by an imaging device, specifying an approximate position of the bed from the region setting image by object detection, and specifying a bed region by extracting a contour of the bed from a local range including the approximate position.

4 Claims, 7 Drawing Sheets (52) U.S. Cl.
CPC ........... *G06T 2207/20081* (2013.01); *G06T 2207/30196* (2013.01)

(58) Field of Classification Search
CPC ........... G06T 2207/20081; H04N 7/18; G06K 9/2054; G06K 9/4609; G06K 9/209; A61B 5/00
See application file for complete search history.

(56) References Cited

U.S. PATENT DOCUMENTS

| | | | |
|---|---|---|---|
| 2014/0036647 A1 | 2/2014 | Yoshizawa et al. | |
| 2014/0267663 A1* | 9/2014 | Yasukawa | G06K 9/00771 348/77 |
| 2016/0171337 A1 | 6/2016 | Okada et al. | |
| 2016/0259969 A1 | 9/2016 | Nabatame et al. | |
| 2017/0014051 A1* | 1/2017 | Matsumoto | A61B 5/742 |
| 2018/0233013 A1* | 8/2018 | Nishikado | H04N 7/18 |
| 2018/0300538 A1* | 10/2018 | Horie | H04N 7/18 |

FOREIGN PATENT DOCUMENTS

| | | |
|---|---|---|
| JP | 2012-71003 A | 4/2012 |
| JP | 2012-71004 A | 4/2012 |
| JP | 2016-112040 A | 6/2016 |
| JP | 2016-158952 A | 9/2016 |
| JP | 2017-38777 A | 2/2017 |

OTHER PUBLICATIONS

Written Opinion issued in International Application No. PCT/JP2017/042584, dated Feb. 20, 2018 (6 pages).

Office Action in counterpart Japanese Patent Application No. 2017-039319 dated Sep. 3, 2019 (4 pages).

Written Submission of Publication issued in Japanese Application No. 2017-039319, dated May 29, 2019 (16 pages).

* cited by examiner

MONITORING ASSISTANCE SYSTEM, CONTROL METHOD THEREOF, AND PROGRAM

TECHNICAL FIELD

The present invention relates to a technique of assisting watching over a subject on a bed.

BACKGROUND ART

In order to prevent a fall accident from a bed, there is a system that assists watching over a patient in a hospital or a nursing facility. Patent Document 1 proposes a system that detects a raising-up action or a getting-out-of-bed action of the patient using an image of a camera installed obliquely above the bed. In this kind of system, the raising-up action or the getting-out-of-bed action of the patient is determined based on a bed region. Thus, it is necessary to previously set (teach) information defining the bed region in the image to the system. However, for a large scale hospital having a large number of beds, manual setting of the bed region is a big burden, which hinders introduction and installation of the system. In addition, because an installation position of the bed in a hospital, a care facility, or the like is not always fixed, but sometimes moved, it is very complicated to manually set the bed region every time the bed is moved. For this reason, Patent Document 2 proposes a method for automatically detecting the bed region from the image.

PRIOR ART DOCUMENTS

Patent Documents

Patent Document 1: Japanese Unexamined Patent Publication No. 2012-071003
Patent Document 2: Japanese Unexamined Patent Publication No. 2016-112040

SUMMARY OF THE INVENTION

Problems to be Solved by the Invention

In the method proposed in Patent Document 2, linear edges are extracted from the image, and a combination of the linear edges considered to constitute a contour of the bed is narrowed down based on a length of each linear edge and a crossing angle between the linear edges. In the method, the accurate detection can be expected for the image, in which the contour of the bed clearly appears and the number of linear edges except for the contour of the bed is small. However, in the case that a part of the contour of the bed is hidden behind a comforter, a candidate of the linear edge constituting the contour of the bed cannot be extracted, and the bed region cannot accurately be detected. In the case that a pattern of a bedspread or the comforter has a linear texture, or in the case that a table or a medical instrument exists around the bed, because many linear edges are extracted in addition to the contour of the bed, there is a possibility that the detection accuracy of the bed region is significantly degraded.

The present invention has been made in view of the above-described circumstances, and an object of the present invention is to provide a technique of accurately detecting the bed region from the image.

Means for Solving the Problem

In order to achieve the above object, the present invention adopts a method for specifying the bed region from a local range after specifying a rough position of the bed from the image by object detection.

Specifically, according to a first aspect of the present invention, a watching assistance system that assists watching over a subject on a bed, the watching assistance system includes: an image acquisition unit configured to acquire an image captured by an imaging device; a region setting unit configured to set at least one determination region in the image based on a bed region; a detector configured to detect the subject from the image acquired by the image acquisition unit; a determination unit configured to determine a state of the subject based on a relationship between the determination region and a position at which the subject is detected; and an output unit configured to provide notification according to a determination result of the determination unit. The region setting unit receives a region setting image from the image acquisition unit, specifies an approximate position of the bed from the region setting image by object detection, and specifies the bed region by extracting a contour of the bed from a local range including the approximate position.

With this configuration, because the detection of the bed region and the setting of the determination region can automatically be performed, the work of introduction and installation of the system is simplified, and the setting is easily changed in the case that the bed or the imaging device is moved, thereby improving convenience of the system. The method for specifying the bed region by extracting the contour of the bed from the local range after specifying the approximate position of the bed by the object detection is adopted as a bed region detection algorithm, so that detection accuracy and a success rate of the bed region can be improved as compared with the conventional method.

Preferably the region setting unit specifies the approximate position of the bed by the object detection using a discriminator in which machine learning of a bed image is performed. This is because the region setting unit has excellent detection accuracy and robustness.

The region setting image may be an image looking down on the entire bed from diagonally above the bed. At this point, the discriminator may detect the entire bed, and the region setting unit may detect a trapezoidal contour from a local range including the entire bed detected by the discriminator. Alternatively, the discriminator may detect a corner of the bed, and the region setting unit may detect a line segment starting at the corner as a contour of the bed from a local range including the corner detected by the discriminator.

The present invention can be recognized as a watching assistance system having at least a part of the above configuration and function or a bed region detection device in the watching assistance system. The present invention can also be recognized as a watching assistance method, a watching assistance system control method, or a bed region detection method including at least a part of the above processing, a program causing a computer to perform these methods, or a computer-readable recording medium in which the program is non-transiently recorded. The above configurations and processes can be combined with each other as long as a technical contradiction is not generated.

Effect of the Invention

In the present invention, the bed region can accurately be detected from the image.

MODES FOR CARRYING OUT THE INVENTION

The present invention relates to a technique of assisting watching over a subject on a bed. The technique can be applied to a system that automatically detects getting-out-of-bed and rising behaviors of the patients or those dependent on care in a hospital or nursing facility, and provides necessary notification when a dangerous state is generated. For example, the system can preferably be used to assist watching over elderly people, patients with dementia, and children.

Hereinafter, an example of a preferred aspect for carrying out the present invention will be described with reference to the drawings. However, a configurations and an operation of a device described in the following embodiment are merely examples, and the scope of the present invention is not limited thereto.

First Embodiment

System Configuration

Figure 1:
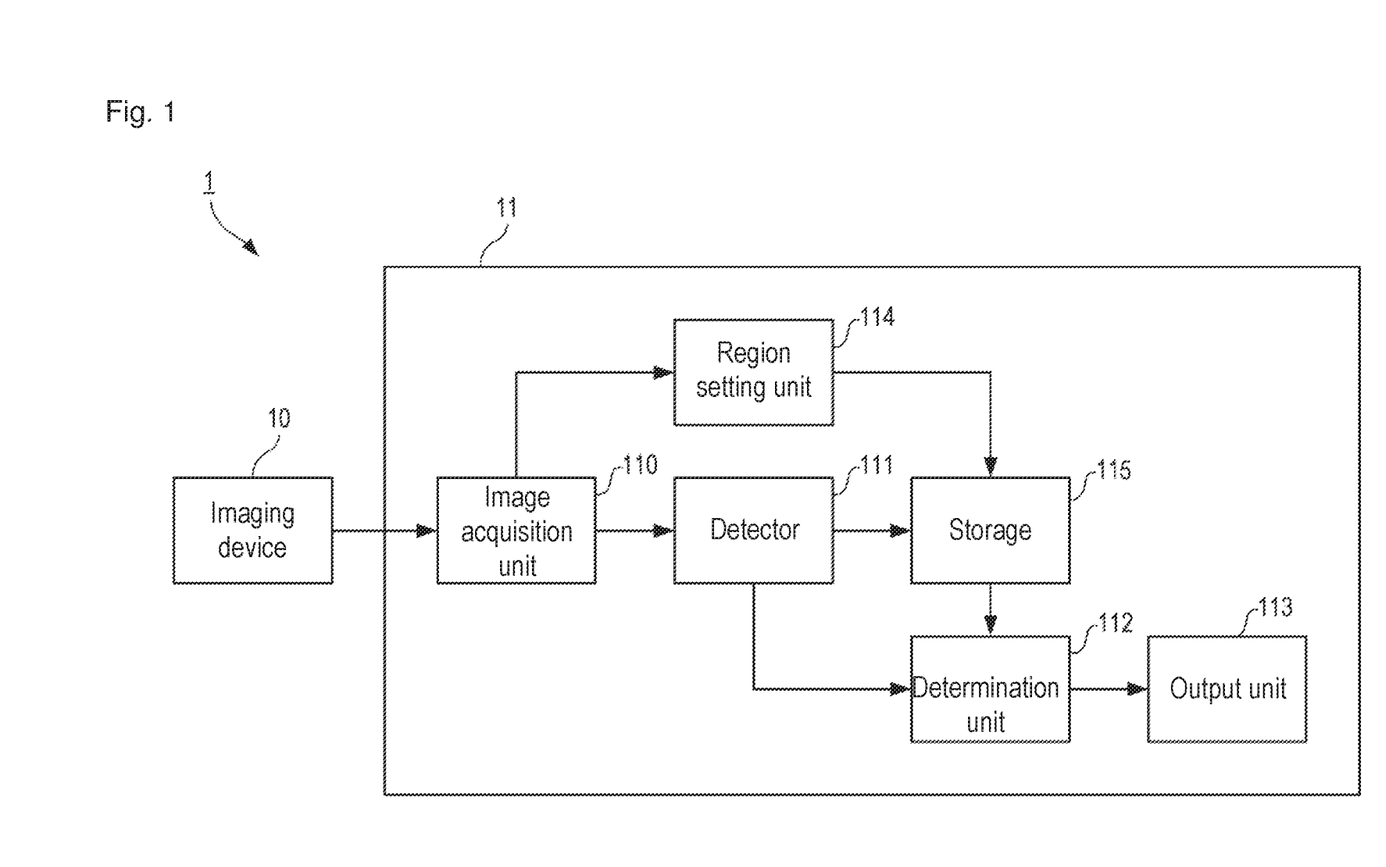
FIG. 1 is a block diagram schematically illustrating a hardware configuration and a functional configuration of a watching assistance system.
Figure 2:
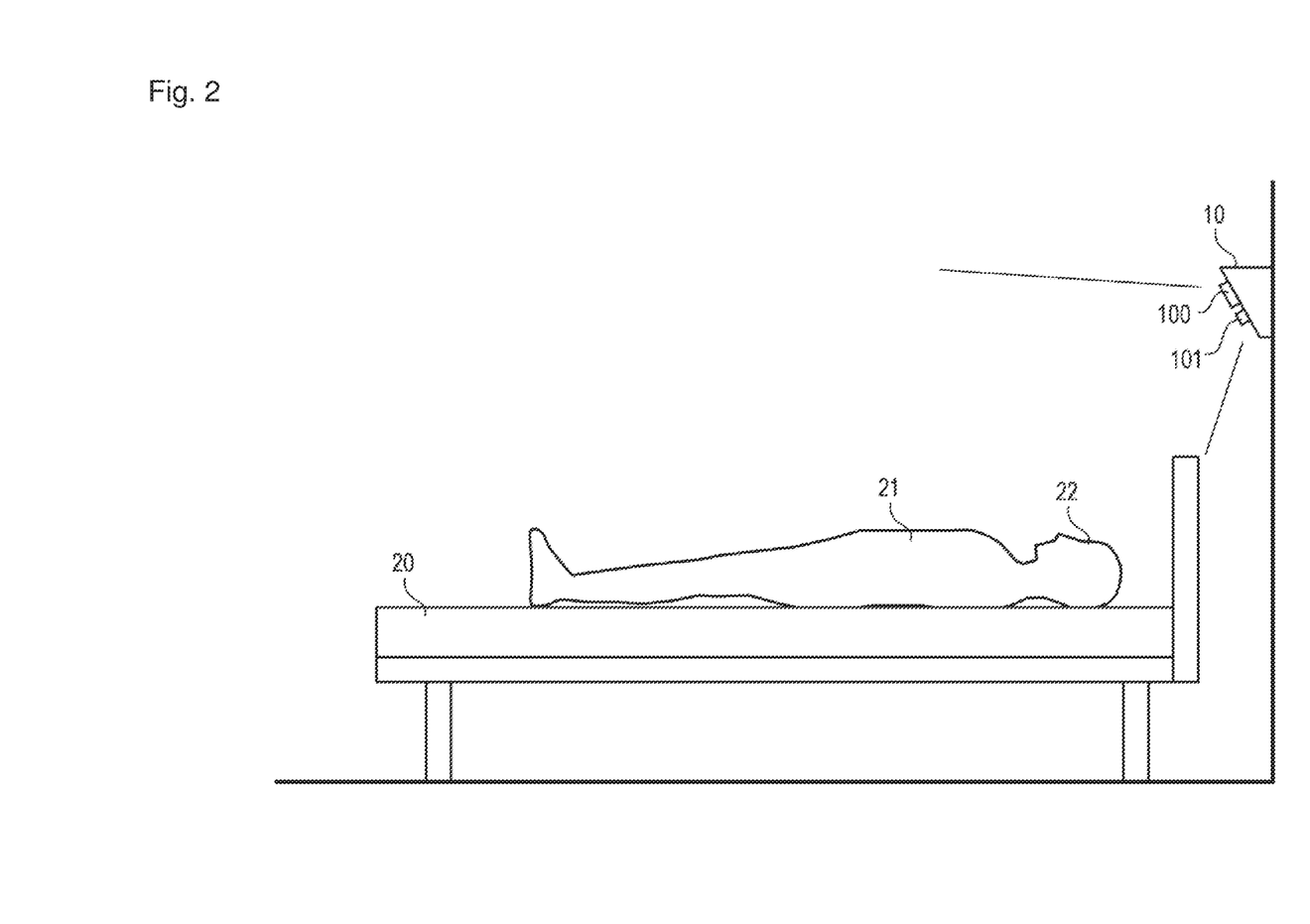
FIG. 2 is a view illustrating an installation example of an imaging device.

A configuration of a watching assistance system according to a first embodiment of the present invention will be described with reference to FIGS. 1 and 2. FIG. 1 is a block diagram schematically illustrating a hardware configuration and a functional configuration of a watching assistance system 1, and FIG. 2 is a view illustrating an installation example of an imaging device.

The watching assistance system 1 includes an imaging device 10 and an information processing device 11 as a main hardware configuration. The imaging device 10 and the information processing device 11 are connected to each other in a wired or wireless manner. Although only one imaging device 10 is illustrated in FIG. 1, a plurality of imaging devices 10 may be connected to the information processing device 11.

The imaging device 10 is a device that images the subject on the bed to capture image data. A monochrome or color visible light camera, an infrared camera, and the like can be used as the imaging device 10. In the embodiment, the imaging device 10 constructed with an infrared LED illumination 100 and a near infrared camera 101 is used in order to enable the watching over the subject even at night (even when a room is dark). As illustrated in FIG. 2, the imaging device 10 is installed to look over an entire bed 20 from an upper side of a head side of a bed 20 toward a foot side. The imaging device 10 captures an image at predetermined time intervals (for example, 10 fps), and the image data is sequentially captured by the information processing device 11.

The information processing device 11 is a device having a function of analyzing the image data captured from the imaging device 10 in real time, automatically detecting a raising-up action or a getting-out-of-bed action of the subject 21 on the bed 20, and providing notification when it is necessary. The information processing device 11 includes an image acquisition unit 110, a detector 111, a determination unit 112, an output unit 113, a region setting unit 114, and a storage 115 as a specific function. The information processing device 11 of the embodiment includes a CPU (processor), a memory, a storage (such as an HDD and an SSD), an input device (such as a keyboard, a mouse, and a touch panel), an output device (such as a display and a speaker), and a communication interface. The CPU executes a program stored in the storage or the memory to implement each function of the information processing device 11. However, the configuration of the information processing device 11 is not limited to this example. For example, distributed computing may be performed by a plurality of computers, a part of the above functions may be performed by a cloud server, or a part of the above functions may be performed by a circuit such as an ASIC or an FPGA.

The image acquisition unit 110 is a function of acquiring the image captured by the imaging device 10. The image data input from the image acquisition unit 110 is temporarily stored in a memory or a storage, and used in processing of the detector 111 or the determination unit 112.

The detector 111 is a function of analyzing the image acquired by the image acquisition unit 110 to detect a predetermined region (such as a head, a face, and an upper body) of the watching subject 21 from the image. Any method may be adopted as a method for detecting a predetermined region from the image. For example, an object detection algorithm using a technique based on a discriminator in which a classic Haar-like feature quantity or HoG feature quantity is used or a technique in which recent Faster R-CNN is used can preferably be used. The detector 111 of the embodiment detects a head (a part above a neck) 22 of the subject 21 by the discriminator in which the Haar-like feature quantity is used, and outputs a position (x, y) and a size (the numbers of vertical and horizontal pixels) of the head 22 as a detection result. For example, the position (x, y) of the head 22 is represented by an image coordinate of a center point of a rectangular frame surrounding the head 22. The detector 111 of the embodiment outputs the detection result in terms of the position and size of an image coordinate system. Alternatively, the detector 111 may convert the image coordinate system into a spatial coordinate system, and output a three-dimensional position or a three-dimensional size in the spatial coordinate system of the subject 21.

The determination unit 112 is a function of making a raising-up determination or a getting-out-of-bed determination of the subject 21 using a detection result of the detector 111. Specifically, based on the detection position of the head 22, the determination unit 112 determines whether the subject 21 raises oneself up, or whether the subject gets out of the bed. A determination algorithm of the determination unit 112 will be described later.

The output unit 113 is a function of providing necessary notification when the determination unit 112 detects the raising-up action or the getting-out-of-bed action of the subject 21. The output unit 113 switches necessity (for example, provides notification only in the case of the dangerous state) of the notification, a notification content (for example, a content of a message), notification means (for example, a voice, a mail, a buzzer, or a warning light), a notification destination (for example, a nurses or a doctor), a notification frequency, and the like according to the danger degree of the action of the subject 21.

The region setting unit 114 is a function of setting a determination region to the image captured by the imaging device 10. In order to monitor the state of the subject 21 on the bed 20, the watching assistance system 1 sets the determination region based on the region of the bed 20 in the image. The watching assistance system 1 of the first embodiment has a function of automatically performing the detection of the bed region and the setting of the determination region using the region setting unit 114, thereby improving convenience of a user. The specific detection algorithm will be described later.

The storage 115 is a function of storing various data used in the processing by the watching assistance system 1. A storage area is provided in the storage 115 in order to store at least various parameters (such as a threshold) used in the raising-up determination or the getting-out-of-bed determination, the setting information about the determination region, image data of a plurality of past frames, or a detection result (used to calculate of the moving speed or the moving direction).

Detection of Bed Region and Setting of Determination Region

Figure 3:
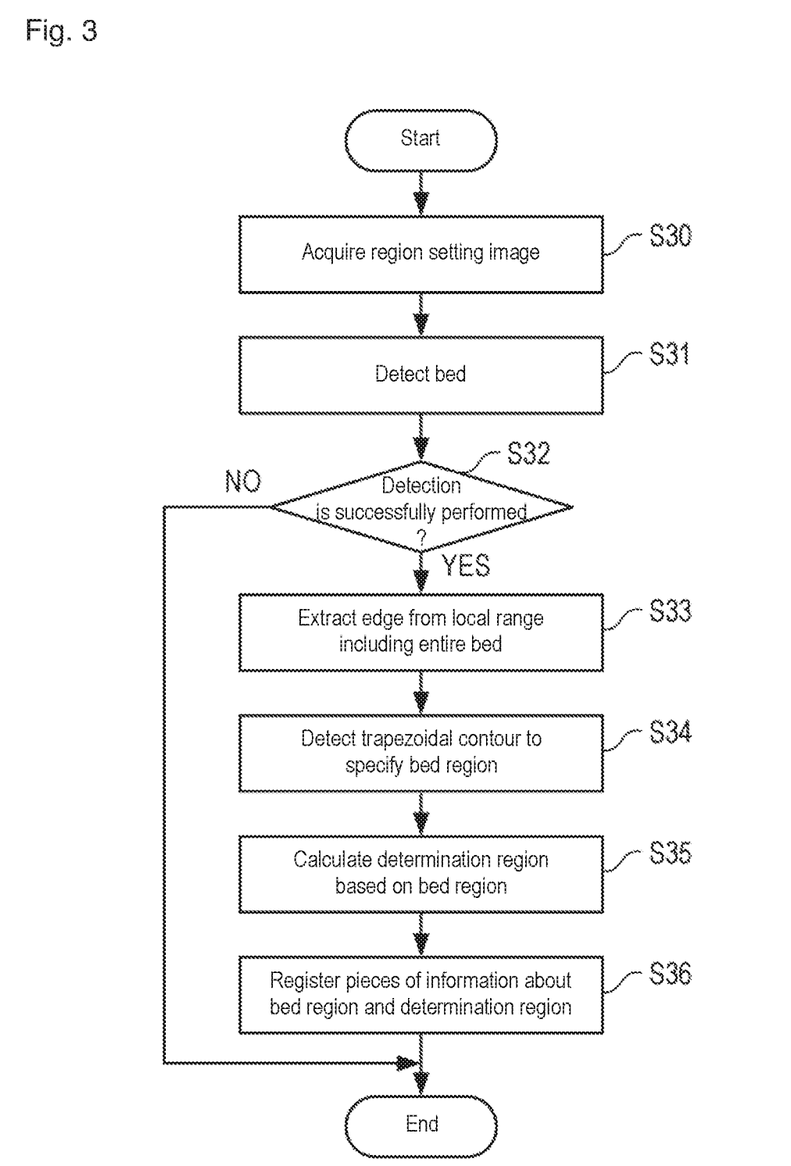
FIG. 3 is a flowchart illustrating region setting processing according to a first embodiment.

Examples of the processing of detecting the bed region and the processing of setting the determination region will be described with reference to FIGS. 3, and 4A to 4D. FIG. 3 is a flowchart illustrating the region setting processing of the first embodiment performed by the information processing device 11, and FIGS. 4A to 4D are examples of the image and the determination region. This processing is performed when the determination region is not set (for example, at time of installation of the watching assistance system 1) or when the determination region needs to be updated with the movement of the bed or the imaging device 10.

Figure 4:
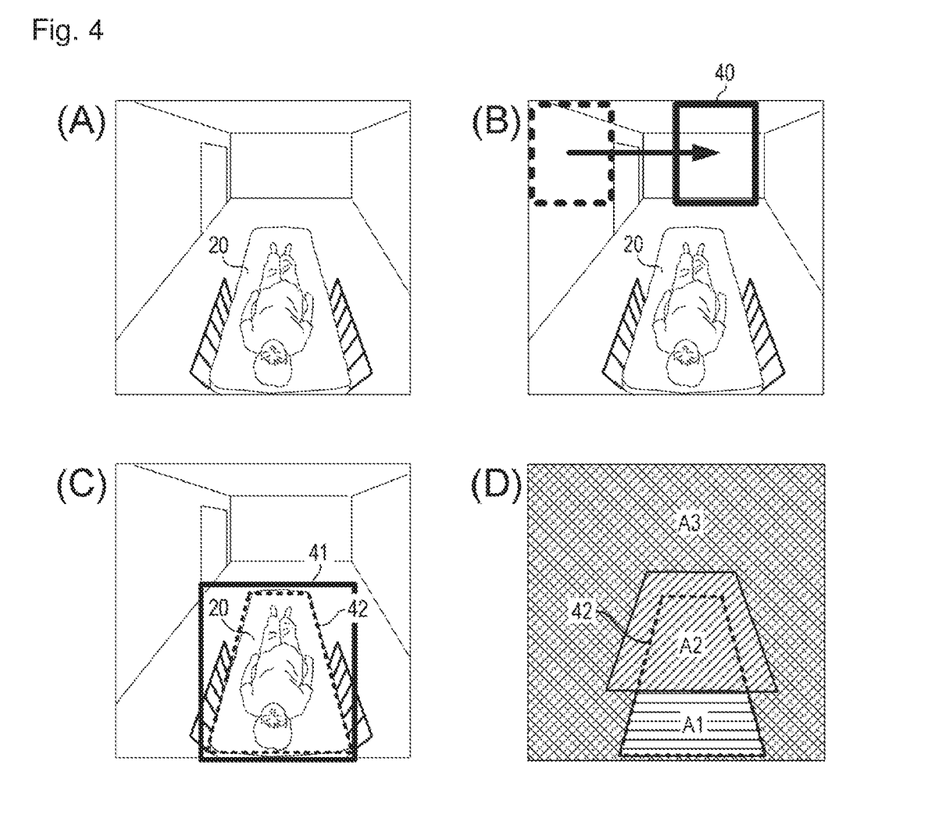
FIGS. 4A to 4D illustrate examples of an image of the region setting processing and a determination region.

In step S30, the image acquisition unit 110 receives a region setting image from the imaging device 10 (FIG. 4A). Preferably the region setting image is an image in which a person or an object does not exist on the bed 20 or an image in which an entire mattress of the bed 20 is exposed, but the region setting image is not necessarily an image in such an ideal state. An image having the same condition as an image captured by watching determination processing (to be described later) may be used as the region setting image.

In step S31, the region setting unit 114 detects the bed from the region setting image. Specifically, as illustrated in FIG. 4B, the processing of evaluating bed-likeness of a partial image in a detection window 40 is repeated while changing the position and size of the detection window 40, thereby detecting the bed 20 having any size existing at any position in the region setting image. The processing in step S31 corresponds to processing of specifying an approximate position of the bed 20 from the region setting image.

Although any object detection algorithm may be used for the detection of the bed, an algorithm using a discriminator in which machine learning of the image of the bed is performed is preferably used from the viewpoint of the detection accuracy and robustness. For example, a discriminator in which a classic Haar-like feature quantity or HoG feature quantity is used or a discriminator in which Deep Learning typified by recent Faster R-CNN is used can preferably be used.

The processing proceeds to step S33 when the bed is successfully detected in step S31 (YES in step S32), and the processing is interrupted when the bed detection fails (NO in step S32).

In step S33, the region setting unit 114 performs an edge extraction processing on a local range 41 including the entire bed 20. A known edge extraction method such as a differential filter or Laplacian filter can be used as the edge extraction. Subsequently, in step S34, the region setting unit 114 detects the contour of the trapezoidal bed 20 from the edge extraction image. A known algorithm such as a Hough transform can be used as the contour detection. As illustrated in FIG. 4C, a region surrounded by the trapezoidal contour (indicated by a broken line) detected in step S34 is set to a bed region 42.

In step S35, the region setting unit 114 sets determination regions A1 to A3 based on the bed region 42 as illustrated in FIG. 4D. The determination region A1 is a region set onto the head side of the bed 20, and corresponds to a range where the head 22 of the subject 21 may exist at a lying time (when the subject 21 lies in the bed 20) (hereinafter, referred to as lying region A1). The determination region A2 is a region set onto the foot side of the bed 20, and corresponds to a range where the head 22 of the subject 21 may exist at a raising-up time (when the subject 21 raises an upper half of the body) (hereinafter, referred to as raising-up region A2). In the first embodiment, positions and sizes of the regions A1, A2 relative to the bed region 42 are previously determined, and the ranges of the regions A1, A2 are determined by calculation when the bed region 42 is specified. The determination region A3 is a region except for the regions A1, A2. When the subject 21 gets out of the bed (when the subject 21 is away from the bed), the head 22 of the subject 21 exists in the region A3 (hereinafter referred to as the getting-out-of-bed region A3).

In step S36, the region setting unit 114 stores the information about the bed region 42 (such as the coordinates and contours of the four corners of the bed region 42) and the information about the regions A1 to A3 (such as the coordinate of an apex of each region) in the storage 115. Then, the setting processing is ended.

Watching Processing

Figure 5:
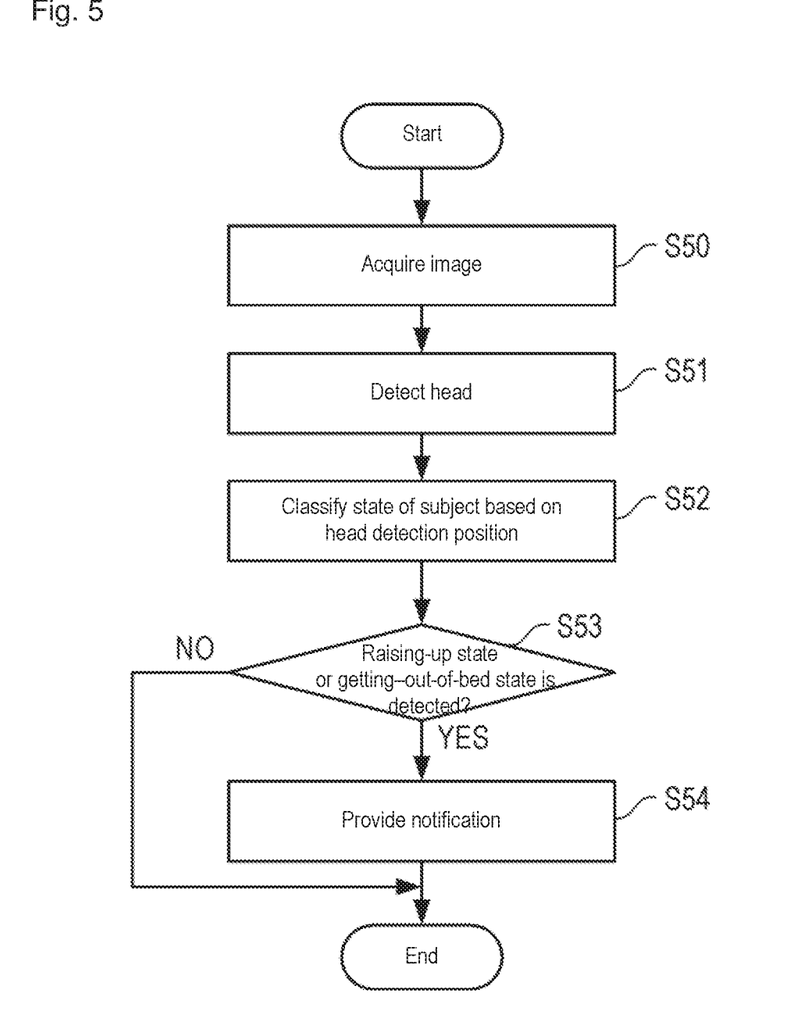
FIG. 5 is a flowchart illustrating watching processing.

An example of the watching processing will be described with reference to FIG. 5. FIG. 5 is a flowchart illustrating the watching processing performed by the information processing device 11. The processing flowchart in FIG. 5 is performed each time the image of one frame is captured from the imaging device 10.

In step S50, the image acquisition unit 110 acquires the image of one frame from the imaging device 10. The acquired image is temporarily stored in the storage 115. Subsequently, the detector 111 detects the head of the subject from the image acquired in step S50 (step S51). Information about the detected head position (xy coordinate) is stored in the storage 115 while correlated with time information about the image or a frame number of the image.

The determination unit 112 determines which one of the regions A1 to A3 the detected position of the head belongs to, and classifies the state of the subject (step S52). At this point, the case that the head is detected in the lying region A1 is referred to as a "lying state", the case that the head is detected in the raising-up region A2 is referred to as a "raising-up state", and the case that the head is detected in the getting-out-of-bed region A3 is referred to as "getting-out-of-bed state". The information about the state of the subject is stored in the storage 115 while correlated with time information or a frame number of the image.

Subsequently, the determination unit 112 compares the state of the subject determined in step S52 to the state of the subject in the previous frame stored in the storage 115, and checks whether the state is changed (step S53). When a change from the lying state to the raising-up state or a change from the raising-up state to the getting-out-of-bed state is detected, the output unit 113 provides notification (step S54). Then, the processing returns to step S50 to continue the monitoring.

In the system of the first embodiment described above, because the detection of the bed region and the setting of the determination region can automatically be performed, the work of introduction and installation of the system is simplified, and the setting is easily changed in the case that the bed or the imaging device is moved, thereby improving convenience of the system. In addition, as a method for detecting the bed area, after the rough position of the bed is specified from the image by object detection, the bed area (bed outline) is specified from the local range. In comparison, the detection accuracy of the bed area and the success rate can be improved. The method for specifying the bed region (the contour of the bed) from the local range after specifying the rough position of the bed from the image by the object detection is adopted as a bed region detection algorithm, so that detection accuracy and a success rate of the bed region can be improved as compared with the conventional method.

Second Embodiment

A second embodiment of the present invention will be described below. The entire bed is detected in the bed region detection of the first embodiment. On the other hand, in the second embodiment, a corner of the bed is detected. The other configurations and pieces of processing are similar to those of the first embodiment. The configuration and processing unique to the second embodiment will be described below.

Figure 6:
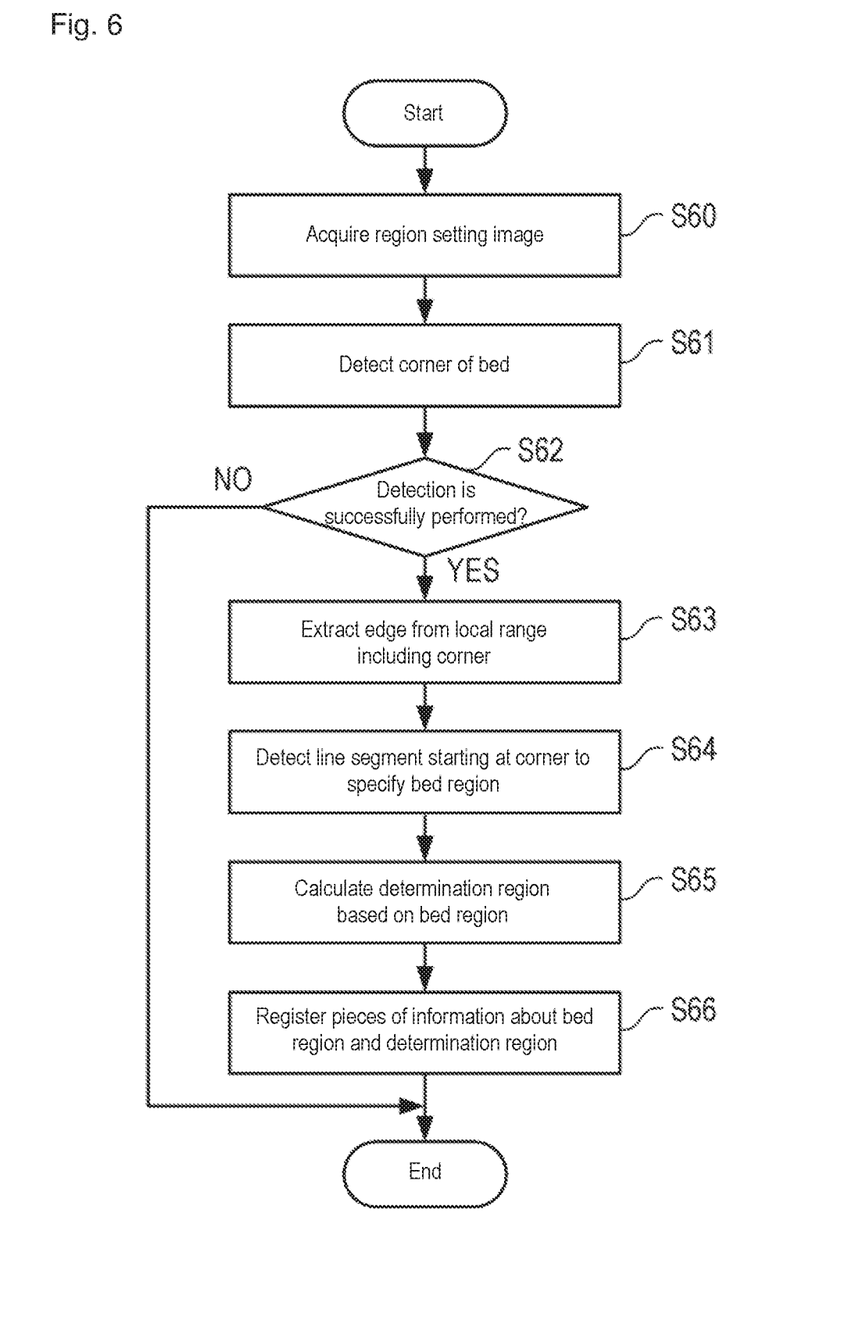
FIG. 6 is a flowchart illustrating region setting processing according to a second embodiment.

Examples of the processing of detecting the bed region and the processing of setting the determination region will be described with reference to FIGS. 6 and 7A to 7D. FIG. 6 is a flowchart illustrating the region setting processing of the second embodiment performed by the information processing device 11, and FIGS. 7A to 7D are examples of the image and the determination region. This processing is performed when the determination region is not set (for example, at time of installation of the watching assistance system 1) or when the determination region needs to be updated with the movement of the bed or the imaging device 10.

Figure 7:
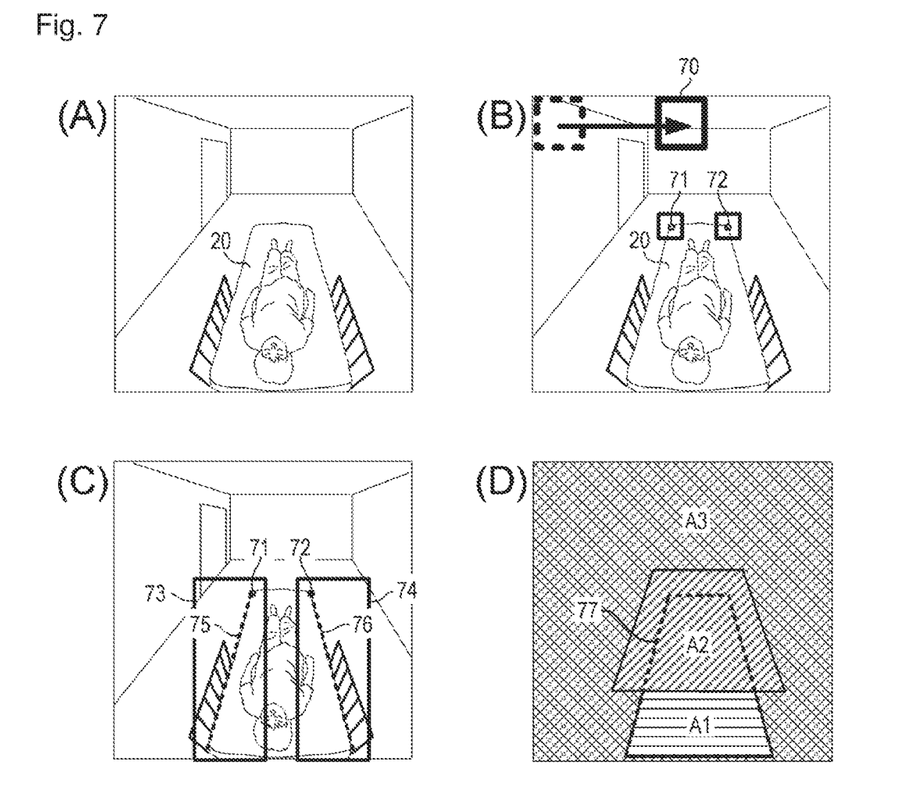
FIGS. 7A to 7D illustrate examples of the image of the region setting processing and the determination region.

In step S60, the image acquisition unit 110 receives the region setting image from the imaging device 10. As illustrated in FIG. 7A, the region setting image may be the same as that used in the first embodiment.

In step S61, the region setting unit 114 detects a corner of the bed from the region setting image. Specifically, as illustrated in FIG. 7B, the processing of evaluating the bed-likeness of the partial image in a detection window 70 is repeated while changing the position and size of the detection window 70, thereby detecting a corner 71 of the bed 20 having any size existing at any position in the region setting image. As a method of detecting a corner, The same technique as the bed detection method described in the first embodiment can be applied to the method of detecting a corner (however, whereas the image used for the machine learning is the image of the entire bed in the first embodiment, the image of the corner of the bed is used in the second embodiment). In the second embodiment, as illustrated in FIG. 7B, right and left corners 71, 72 on the foot side of the bed 20 are detected using two kinds of discriminators. The processing in step S61 corresponds to processing of specifying an approximate position of the bed 20 from the region setting image.

The processing proceeds to step S63 when the two corners 71, 72 are successfully detected in step S61 (YES in step S62), and the processing is interrupted when the bed detection fails (NO in step S62).

In step S63, the region setting unit 114 sets local ranges 73, 74 including the corners 71, 72, and performs edge extraction processing on the local ranges 73, 74. A known edge extraction method such as a differential filter or Laplacian filter can be used as the edge extraction. Subsequently, in step S64, the region setting unit 114 detects line segments 75, 76 (indicated by broken lines) extending downward from the edge extraction image starting at the corners 71, 72. A known algorithm such as a Hough transform can be used as the line segment detection. A region surrounded by a trapezoidal contour defined by the two corners 71, 72 and the two line segments 75, 76 is set as a bed region 77. The subsequent pieces of processing (steps S65, S66) are the same as steps S35, S36 of the first embodiment, so that the description will be omitted.

In the system of the second embodiment described above, the same function and effect as those of the first embodiment can also be obtained.

Others

The descriptions of the embodiments merely illustrate the present invention. The present invention is not limited to the above specific aspects, but various modifications can be made without departing from the scope of the technical idea thereof. For example, in the above embodiment, the entire bed or the corner is detected, but the outline of the bed can be obtained by detecting other features of the bed (for example, the side end of the bed, the end on the foot side or the head side). The position may be specified. A number and a shape of the determination regions can arbitrarily be designed. Although the head is the detection target in the embodiments, a region (such as a face, a part (facial organ) of the face, and an upper body) except for the head may be the detection target.

DESCRIPTION OF SYMBOLS 1 watching assistance system
10 imaging device
11 information processing device
110 image acquisition unit
111 detector
112 determination unit
113 output unit
114 region setting unit
115 storage
100 illumination
101 near infrared camera
20 bed
21 subject
22 head 40 detection window
41 local region
42 bed region
A1 lying region
A2 raising-up region
A3 getting-out-of-bed region
70 detection window
71, 72 corner
73, 74 local region
75, 76 line segment
77 bed region

The invention claimed is:

1. A watching assistance system that assists watching over a subject on a bed, the watching assistance system comprising:
    an image acquisition unit configured to acquire an image captured by an imaging device;
    a region setting unit configured to set at least one determination region in the image based on a bed region;
    a detector configured to detect the subject from the image acquired by the image acquisition unit;
    a determination unit configured to determine a state of the subject based on a relationship between the determination region and a position at which the subject is detected; and
    an output unit configured to provide notification according to a determination result of the determination unit,
    wherein the region setting unit
    receives a region setting image looking down on the entire bed from diagonally above the bed, from the image acquisition unit,
    detects two corners of the bed from the region setting image by object detection,
    sets two local ranges respectively including the two corners,
    detects a line segment starting at a corner in a local range, for each of the two local ranges, and
    specifies, as the bed region, a region surrounded by a quadrangular contour defined by two corners and two line segments.

2. The watching assistance system according to claim 1, wherein the region setting unit detects the corner of the bed by the object detection using a discriminator in which machine learning of a bed image is performed.

3. A method for controlling a watching assistance system that assists watching over a subject on a bed, the watching assistance system control method comprising:
    a step of acquiring an image captured by an imaging device;
    a step of setting at least one determination region in the image based on a bed region;
    a step of detecting the subject from the acquired image;
    a step of determining a state of the subject based on a relationship between the determination region and a position at which the subject is detected; and
    a step of providing notification according to a determination result of the state of the subject,
    wherein the determination region setting step includes:
    a step of receiving a region setting image looking down on the entire bed from diagonally above the bed, from the image acquisition unit;
    a step of detecting two corners of the bed from the region setting image by object detection;
    a step of setting two local ranges respectively including the two corners;
    a step of detecting a line segment starting at a corner included in a local range, for each of the two local ranges; and
    a step of specifying, as the bed region, a region surrounded by a quadrangular contour defined by two corners and two line segments.

4. A program causing a computer to perform each step of the watching assistance system control method according to claim 3.

* * * * *